US00PP09011P

United States Patent [19]

Kordes

[11] Patent Number: Plant 9,011

[45] Date of Patent: Dec. 13, 1994

[54] SHRUB ROSE PLANT NAMED KORSAKU

[75] Inventor: Wilhelm Kordes, Sparrieshoop, Germany

[73] Assignee: Bear Creek Gardens, Inc., Medford, Oreg.

[21] Appl. No.: 201,238

[22] Filed: Feb. 24, 1994

[51] Int. Cl.[5] ..... A01H 5/00

[52] U.S. Cl. ..... Plt./1

[58] Field of Search ..... Plt. 1, 26

U.S. PATENT DOCUMENT

PLT 340 9/1939 Prior ..... PLT/26

*Primary Examiner*—Howard J. Locker

*Attorney, Agent, or Firm*—Klarquist Sparkman Campbell Leigh & Whinston

[57] ABSTRACT

Rose plant of the shrub class having disease-resistant, Rugosa-like foliage; repeat bloom, spreading habit of growth; and numerous, narrow, sharp thorns.

1 Drawing Sheet

The present invention relates to a new and distinct variety of rose plant of the shrub class which was originated by me by crossing the variety "The Fairy" (unpatented) with an unnamed, unpatented seedling.

The primary objective of this breeding was to produce a new rose variety having the spreading habit, repeat bloom and disease resistance of the female parent combined with the Rugosa-like foliage and disease resistance of the male parent. The objective was substantially achieved, along with other desirable improvements, as evidenced by the following unique combination of chartacteristics that are outstanding in the new variety and that distinguish it from its parents, as well as from all other varieties of which I am aware:

1. A spreading habit of growth;
2. Rugosa-like foliage;
3. Disease resistance;
4. Repeat flowering; and
5. Narrow, numerous sharp thorns.

Asexual reproduction of this new variety by budding and by softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—The Fairy.

*Pollen parent.*—Unnamed seedling.

Classification:

*Botanical.*—*Rosa hybrida.*

*Commercial.*—Shrub.

FLOWER

Observations made from specimens grown in garden environments in Somis, Calif., and Sparrieshoop, Germany.

Blooming habit: Recurrent.

Bud:

*Size.*—13 to 19 mm in length when the petals start to unfurl.

*Form.*—Short, pointed ovoid.

*Color.*—When sepals first divide, bud color is Red Group 52C. When half blown, the upper and lower sides of the petals are Red Group 52D.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Pear. Size: Small (3 mm×3 mm). Surface: Smooth.

*Peduncle.*—Length: Short (4 cm). Surface: Very hairy with occasional glands. Color: Light green. Strength: Stiff, slender.

Bloom:

*Size.*—Small. Average open size is 2 to 2½ inches in diameter.

*Borne.*—Several together in rounded clusters.

*Stems.*—Short (6 to 8 inches); strong.

*Form.*—When first open: Cupped. Permanence: Becoming flat.

*Petalage.*—Number of petals under normal conditions: 5.

*Color.*—The upper and reverse sides of the petals are Red Group 52 D. The major color on the upper side is Red Group 52 D.

*Variegations.*—None.

*Discoloration.*—The general tonality at the end of the first and third days: No change.

*Fragrance.*—Moderate.

Petals:

*Texture.*—Thin.

*Shape.*—Oval.

*Form.*—Flat.

*Arrangement.*—Imbricated, with no petaloids in the center.

*Persistence.*—Drop off cleanly.

*Lastingness.*—On the plant: Short (3 to 4 days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Gold Yellow.

*Styles.*—Color: Greenish white with some pink as the style joins the stigma.

*Stigmas.*—Color: Greenish white.

Form: Shrub.

Growth: Vigorous, branching, sprawling. At maturity, without pruning (3 years old), it will reach 1.2 meters tall and spread 1.5 to 1.8 meters wide. Normally, if pruned, it will be 76 cm tall and 100 cm wide.

Foliage: Number of leaflets on normal mid-stem leaves: 7 or 9.

*Size.*—Medium (11 cm×5 cm).

*Quantity.*—Abundant.

*Color.*—New foliage: Green Group 141A. Old foliage: Green Group 137A.

Leaflets:

*Shape.*—Pointed oval.

*Texture.*—Upper side: Leathery, glossy, rough (Rugosa-like).

*Edge.*—Serrated.

*Serration.*—Single.

*Petiole rachis.*—Color: Green.

*Petiole underside.*—Rough, with prickles.

*Stipules.*—Medium (13 mm), bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—Many on main canes from base. Many on laterals from main canes.

*Form.*—Medium (3 mm to 9 mm), narrow, very sharp, hooked downward.

*Color when young.*—Green.

Small Prickles:

*Quantity.*—Many on main stalks and laterals.

*Color.*—Green.

I claim:

1. A new and distinct variety of rose plant of the shrub class, substantially as herein shown and described, characterized particularly as to novelty by its disease-resistant, Rugosa-like foliage; repeat bloom, spreading habit of growth; and numerous, narrow, sharp thorns.

* * * * *

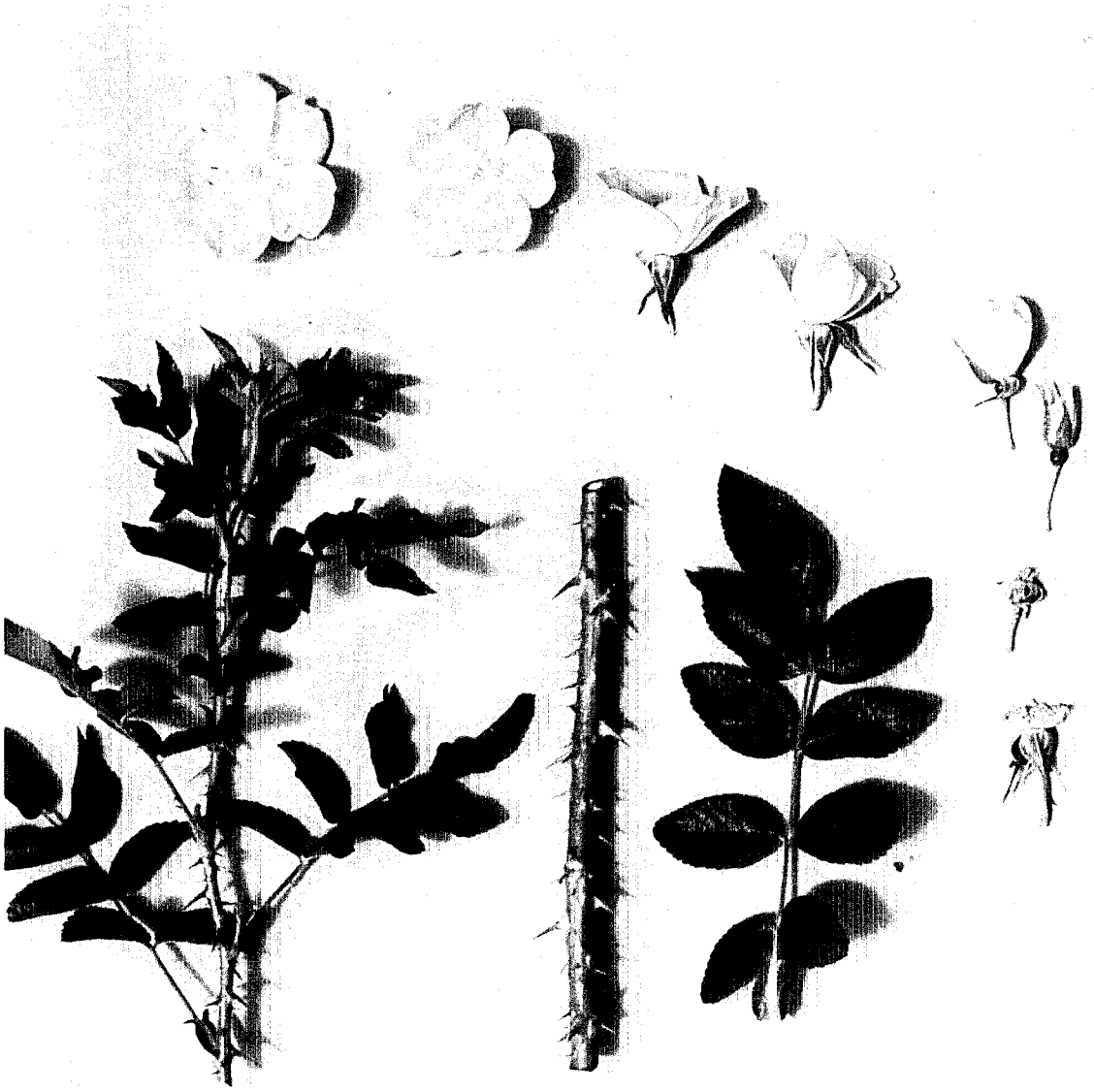
KORsaku